United States Patent [19]

Chan

[11] Patent Number: 5,723,452
[45] Date of Patent: Mar. 3, 1998

[54] THERAPEUTIC BENZONITRILES

[75] Inventor: Joseph Howing Chan, Chapel Hill, N.C.

[73] Assignee: Glaxo Wellcome Inc., RTP, N.C.

[21] Appl. No.: 696,999

[22] PCT Filed: Feb. 23, 1995

[86] PCT No.: PCT/GB95/00375

§ 371 Date: Aug. 21, 1996

§ 102(e) Date: Aug. 21, 1996

[87] PCT Pub. No.: WO95/23133

PCT Pub. Date: Aug. 31, 1995

[30] Foreign Application Priority Data

Feb. 23, 1994 [GB] United Kingdom ............... 9403449

[51] Int. Cl.⁶ ..................... A61K 31/63; C07C 255/34
[52] U.S. Cl. .................... 514/155; 558/413; 558/418
[58] Field of Search ................... 558/413, 418; 514/155

[56] References Cited

U.S. PATENT DOCUMENTS 4,829,058  5/1989  Seydel et al. ...................... 514/155

FOREIGN PATENT DOCUMENTS 0 034 263  8/1981  European Pat. Off. .
0 507 488  10/1992  European Pat. Off. .
WO 92/00952  1/1992  WIPO .
WO 92/06683  4/1992  WIPO .

OTHER PUBLICATIONS

Harris, N.V. et al., "Antifolate and Antibacterial Activities of 5-Substituted 2,4-Diamonoquinazolines", J. Med Chem, vol. 33, No. 1, 1990, pp. 434–444.

Ashton, W.T. et al., "Synthesis of 5-Substituted Quinazolines as Potential Antimalarial Agents", J. Med. Chem., vol. 16, No. 11, 1973, pp. 1233–1237.

*Primary Examiner*—Johann Richter
*Assistant Examiner*—Ebenezer Sackey
*Attorney, Agent, or Firm*—LaVonda R. DeWitt

[57] ABSTRACT

The present invention relates to novel compounds of formula (I):

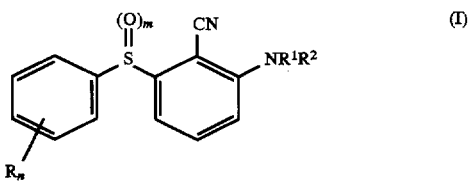

or a physiologically functional derivative thereof, pharmaceutical formulations containing them, processes for their preparation and their use in therapy for the prophylaxis or treatment of HIV infection or inflammation are disclosed.

14 Claims, No Drawings

THERAPEUTIC BENZONITRILES

This application is a 371 of PCT/GB95/00375, filed Feb. 23, 1995.

The present invention relates to certain arylthiobenzonitrile compounds, processes for their preparation, pharmaceutical formulations containing them and their use in therapy, particularly for the prophylaxis or treatment of viral infections and inflammation.

In the field of antiviral chemotherapy, few drugs exist which effectively combat the virus per se, owing to the difficulty of attacking the virus while leaving uninfected host cells unimpaired. It has been established that certain stages in the virus replicative cycle offer possible targets for antiviral therapy. These stages may prove susceptible to attack where they differ sufficiently from any corresponding host-cell function. However, owing to great similarity between viral and host functions, effective treatments have proved very difficult to identify.

One group of viral pathogens which has assumed a particular importance is the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome my be incorporated into the host cell genome, allowing it to take advantage of the host cell's transcription/translation machinery for the purposes of replication. Once incorporated, the viral DNA is virtually indistinguishable from the host's DNA and, in this state, the virus introducing mechanism may persist for the life of the cell.

A species of retrovirus, Human Immunodeficiency Virus (HIV), has been reproducibly isolated from humans with Acquired Immune Deficiency Syndrome (AIDS) or with the symptoms that frequently precede AIDS. AIDS is an immunosuppressive or immunodestructive disease that predisposes subjects to fatal opportunistic infections. Characteristically, AIDS is associated with a progressive depletion of T-cells, especially the helper-inducer subset bearing the OKT$^4$ surface marker. HIV is cytopathic and appears to preferentially infect and destroy T-cells bearing the OKT$^4$ marker. It is now generally recognised that HIV is the aetiological agent of AIDS.

PCT patent application WO 92/06683 discloses certain diphenylsulfides having anti-retrovirus activity. However, there is no disclosure of the compounds of formula (I) infra. 2-Amino-6-(phenylthio)benzonitrile is disclosed as a chemical intermediate (Ashton, W. T. et al., *J. Med. Chem.*, 1973, 16(11) 1233–7 and Harris, N. V. et al., *J. Med. Chem.* 1990, 33(1), 434–4).

We have now identified certain arylthiobenzonitrile compounds and salts thereof which have unexpectedly been found suitable for use in medical therapy and in particular as antiviral and antiinflammatory agents.

According to the first aspect of the present invention there is provided a compound of formula (I)

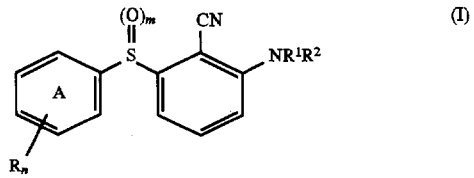

wherein,

R is hydrogen, $C_{1-4}$ alkyl (for example methyl), $C_{1-4}$ alkoxy (for example methoxy), hydroxyl, mercapto, or a group of formula $NR^{1a}R^{2a}$ or $SR^{1a}$ (wherein $R^{1a}$ and $R^{2a}$, which may be the same or different, are hydrogen, $C_{1-4}$ alkyl (for example methyl) or phenyl $C_{1-4}$ alkyl (for example benzyl));

$R^1$ and $R^2$, which may be the same or different, are hydrogen, $C_{1-4}$ alkyl (for example methyl) or phenyl $C_{1-4}$ alkyl (for example benzyl);

m is 0, 1 or 2; and n is 1 to 5 (when n is greater than 1, R may be the same or different); provided that when $R^1$ and $R^2$ are both hydrogen and m is 0, R is not hydrogen; or a physiologically functional derivative thereof.

Preferably both $R^1$ and $R^2$ are hydrogen or $C_{1-4}$ alkyl, or $R^1$ is hydrogen and $R^2$ is $C_{1-4}$ alkyl.

Preferred compounds of formula (I) include those wherein n is 1 or 2, ring A is 3-substituted or 3,5-disubstituted and m is 2.

Preferred compounds of formula (I) include:

(1) 2-amino-6-[(3-methoxyphenyl)thio]benzonitrile;
(2) 2-amino-6-[(3-methylphenyl)thio]benzonitrile;
(3) 2-amino-6-[(3,5-dimethylphenyl)thio]benzonitrile;
(4) 2-amino-6-[(3-aminophenyl)thio]benzonitrile;
(5) 2-amino-6-[(3,4-dimethoxyphenyl)thio]benzonitrile;
(6) 2-amino-6-[(3-methoxyphenyl)sulfonyl]benzonitrile;
(7) 2-amino-6-[(3-methoxyphenyl)sulfinyl]benzonitrile;
(8) 2-amino-6-[(3,5-dimethylphenyl)methyl]benzonitrile;
(9) 2-amino-6-[(3,5-dimethylphenyl)sulfonyl]benzonitrile;
(10) 2-amino-6-[(3-methyl-5-methoxyphenyl)sulfonyl]benzonitrile;
(11) 2-amino-6-[(3-methyl-5-methoxyphenyl)thio]benzonitrile; and
(12) 2-(benzylamino)-6-[(3,5-dimethylphenyl)sulfonyl]benzonitrile;

or a physiologically functional derivative thereof.

A preferred physiologically functional derivative of a compound of formula (I) is N-[2-cyano-3-[(3,5-dimethylphenyl)sulfonyl]]-2,2,2-trifluoroacetamide.

A particularly preferred compound of formula (I) is 2-amino-6-[(3,5-dimethylphenyl)sulfonyl]benzonitrile.

The compounds of formula (I) and also the known compound, 2-amino-6-(phenylthio)benzonitrile, and their physiologically functional derivatives thereof are hereinafter referred to as the compounds according to the invention.

Compounds according to the invention are of particular use in the treatment or prophylaxis of HIV infections. Compounds according to the invention also have antiinflammatory properties.

In another aspect of the present invention there are provided the compounds according to the invention for use in medical therapy, more particularly for use as antiviral agents, for example, for the prophylaxis or treatment of a retrovirus infection such as a HIV infection.

The present invention further includes:

(a) A method for the prophylaxis or treatment of a viral infection in particular a HIV infection in an injected host, for example, a mammal including a human, which comprises administering to said host a therapeutically effective non-toxic amount of a compound according to the invention.

(b) Use of a compound according to the invention in the manufacture of a medicament for the prophylaxis or treatment of a viral infection, in particular an HIV infection.

In a further aspect of the invention there are provided the compounds according to the invention for use as an antiinflammatory agents.

The present invention further includes:

(c) A method for the prophylaxis or treatment of inflammation in an affected host, for example, a mammal including a human, which comprises administering to said host a therapeutically effective non-toxic mount of a compound according to the invention, (d) Use of a compound according to the invention in the manufacture of a medicament for the prophylaxis or treatment of inflammation.

By the term "inflammation" it is meant the reactive state of hyperemia and exudation from blood vessels, with consequent redness, heat, swelling and pain, which a tissue undergoes in response to physical or chemical injury or bacterial or vital invasions.

Thus the compounds according to the invention are useful for treating inflammatory conditions associated with disorders such as arthritis, tendinitis, synovitis, bursitis and inflammatory bowel disease.

Examples of clinical conditions caused by HIV infections which may be treated in accordance with the invention include Acquired Immune Deficiency Syndrome (AIDS) or symptoms that frequently precede AIDS, or related clinical conditions such as AIDS-related complex (ARC), progressive generalised lymphadenopathy (PGL), Kaposis sarcoma, thrombocytopenic purpura, AIDS related neurological conditions, such as multiple sclerosis or tropical paraparesis and also anti-HIV antibody-positive and HIV-positive conditions including AIDS asymptomatic patients.

As used herein, the term "physiologically functional derivative" means any physiologically acceptable salt, ester, amide, salt of such ester, or solvate of any thereof of a compound of formula (I) or any other compound which upon administration to the recipient is capable of providing directly or indirectly such a compound or a therapeutically active metabolite or residue thereof.

Preferred esters of the compounds of formula (I), wherein R is hydroxyl, included within the scope of the invention as physiologically functional derivatives include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy or amino); sulfonate esters, such as alkyl- or aralkylsulfonyl (for example, methanesulfonyl); amino acid esters (for example, L-valyl or L-isoleucyl); and mono-, di-, or tri-phosphate esters. In such esters, unless otherwise specified, any alkyl moiety present advantageously contains from 1 to 18 carbon atom, particularly from 1 to 6 carbon atom, more particularly from 1 to 4 carbon atoms. Any cycloalkyl moiety present in such esters advantageously contains from 3 to 6 carbon atoms. Any aryl moiety present in such esters advantageously comprises an optionally substituted phenyl group. Any reference to any of the above compounds also includes a reference to a pharmaceutically acceptable salt thereof.

The above-mentioned physiologically acceptable amides of the compounds of the invention are those derivatives wherein an amino group is present in the form of an amide, e.g., —NHCOR wherein R is $C_{1-6}$ alkyl, trihalomethyl (e.g., trifluoromethyl) or aryl (e.g., phenyl optionally substituted by halogen, $C_{1-4}$ alkyl, $C_{1-4}$ alkoxy, nitro or hydroxyl).

Examples of pharmaceutically acceptable salts of the compounds of the invention and of physiologically acceptable derivatives thereof include salts derived from an appropriate base, such as an alkali metal (for example, sodium), an alkaline earth metal (for example, magnesium), ammonium and $NX_4^+$ (wherein X is $C_{1-4}$alkyl). Pharmaceutically acceptable salts include salts of organic carboxylic acids such as acetic, fumaric, citric, lactic, tartaric, maleic, malic, isethionic, lactobionic and succinic acids; organic sulfonic acids such as methanesulfonic, ethanesulfonic, benzenesulfonic and p-toluenesulfonic acids and inorganic acids such as hydrochloric, hydrobromic, sulfuric, phosphoric and sulfamic acids.

For therapeutic use, salts of the compounds of the invention will be pharmaceutically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived from a physiologically acceptable acid or base, are within the scope of the present invention.

The compounds according to the invention may be employed alone or in combination with other therapeutic agents for the treatment of HIV infections, such as Nucleoside Reverse Transcriptase Inhibitors (NRTIs) for example zidovudine, zalcitabine, didanosine, lamivudine, stavudine, 5-chloro-2'-3'-dideoxy-3'-fluouridine and (2R,5S)-5-fluoro-1-[2-(hydroxymethyl)-1,3-oxathiolan-5-yl]cytosine, non-NRTIs for example nevirapine and α-APA, HIV-proteinase inhibitors for example saquinavir and VX-478, other anti-HIV agents for example soluble CD4, immune modulators for example interleukin II, erythropoetein, tucaresol and interferons for example α-interferon. The component compounds of such combination therapy may be administered simultaneously, in either separate or combined formulations, or at different times, for example, sequentially, such that a combined effect is achieved.

The present invention further provides pharmaceutical formulations of the compounds according to the invention, also referred to herein as active ingredients, which may be administered for therapy to a mammal including a human ("the recipient") by any suitable route appropriate to the clinical condition to be treated; suitable routes include oral, rectal, nasal, topical (including buccal, sublingual and transdermal), vaginal and parenteral (including subcutaneous, intramuscular, intravenous and intradermal). It will be appreciated that the preferred route will vary with the condition, weight, age and sex of the recipient, the nature of the infection and the chosen active ingredient.

The amount of a compound of the invention required for the treatment of the above named vital infections and for the treatment of inflammatory conditions, will depend on a number of factors including the severity of the condition to be treated and the identity of the recipient and will ultimately be at the discretion of the attendant physician.

In general, a suitable dose for the treatment of a viral infection in a human is in the range of 3.0 to 120 mg per kilogram body weight of the recipient per day, preferably in the range of 6 to 90 mg per kilogram body weight per day and most preferably in the range of 15 to 60 mg per kilogram body weight per day. For the treatment of inflammation, a suitable dose for a human is in the range of 0.1 to 100 mg/kg body weight of the recipient per day, preferably 0.5 to 50 mg/kg per day and most preferably 1 to 20 mg/kg per day.

Unless otherwise indicated all weights of active ingredients are calculated as the parent compound of the invention. In the case of a physiologically functional derivative of a compound of the invention or a pharmaceutically acceptable salt or a solvate of any thereof the figures would be increased proportionately. The desired dose is preferably presented as two, three, four, five, six, or more sub-doses administered at appropriate intervals throughout the day. These sub-doses may be administered in unit dosage forms, for example, containing from 10 to 1500 mg, preferably from 20 to 1000 mg, most preferably from 50 to 700 mg of active ingredient per unit dosage form. Alternatively, if the condition of the recipient so requires, the dose may be administered as a continuous infusion.

While it is possible for the active ingredient to be administered alone, it is preferable to present it as a pharmaceutical formulation. The formulations of the present invention comprise at least one active ingredient, as defined above, together with one or more acceptable carriers therefor and, optionally, one or more other therapeutic agents. Each carrier must be "acceptable" in the sense of being compatible with the other ingredients of the formulation and not injurious to the patient.

Formulations of the invention include those suitable for administration by any of the aforementioned routes which may conveniently be presented in unit dosage form and may be prepared by any method well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers, or both, and then, if necessary, shaping the product.

Formulations of the present invention suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary, or paste or may be contained within liposomes.

A tablet may be made by compression or moulding, optionally with one or more accessory ingredients. Compressed tablets may be prepared by compressing in a suitable machine the active ingredient in a free-flowing form such as a powder or granules, optionally mixed with a binder (for example, povidone, gelatin, hydroxypropylmethyl cellulose), lubricant, inert diluent, preservative, disintegrant (for example, sodium starch glycollate, cross-linked povidone, cross-linked sodium carboxmethyl cellulose), or a surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using for example, hydroxypropylmethyl cellulose in varying proportions to provide the desired release profile or to be soluble or effervescent when added to liquid. Tablets may optionally be provided with an enteric coating, to provide release in parts of the gut other than the stomach.

A capsule my be made by filling a loose or compressed powder on an appropriate filling machine, optionally with one or more additives. Examples of suitable additives include binders such as povidone; gelatin, lubricants, inert diluents and disintegrants as for tablets. Capsules may also be formulated to contain pellets or discrete sub-units to provide slow or controlled release of the active ingredient. This can be achieved by extruding and spheronising a wet mixture of the drug plus an extrusion aid (for example microcrystalline cellulose) plus a diluent such as lactose.

The spheroids thus produced can be coated with a semipermeable membrane (for example ethyl cellulose, Eudragit WE30D) to produce sustained release properties.

Pharmaceutical formulations for topical administration according to the present invention may be formulated as an ointment, cream, suspension, lotion, powder, solution, paste, gel, spray, aerosol or oil. Alternatively, a formulation may comprise a dressing such as a bandage or adhesive plaster impregnated with active ingredients and optionally one or more excipients or diluents.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution of 2) dissolved in an adhesive or 3) dispersed in a polymer. A suitable concentration of the active compound is about 1% to 35%, preferably about 3% to 15%. As one particular possibility, the active compound may be delivered from the patch by ionophoresis as generally described in Pharmaceutical Research, 3(6), 318 (1986).

For infections of the eye or other external tissues, for example mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base or as a water-in-oil base.

If desired, the aqueous phase of the cream base may include, for example, at least 40–45% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may include a compound which enhances absorption or penetration of the active ingredient through the skin or other affected areas. Examples of such dermal penetration enhancers include dimethylsulphoxide and related analogues.

The oily phase of an emulsion formulation according to the invention may comprise merely an emulsifier (otherwise known as an emulgent), but desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. The cream should preferably be a non-greasy, non-staining and washable product with suitable consistency to avoid leakage from robes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP my be used, the last three being preferred esters. These may be used alone or in combination depending on the properties required. Alternatively, high melting point lipids such as white soft paraffin and/or liquid paraffin or other mineral oils can be used.

Formulations suitable for topical administration in the mouth include lozenges comprising the active ingredient in a flavored material, usually sucrose and acacia or tragacanth.

Formulations for rectal administration may be presented as a suppository with a suitable base comprising for example cocoa butter or higher fatty alcohol (e.g. hard wax, European Pharmacopoeia) or triglycerides and saturated fatty acids (e.g. Witepsol).

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or sub-dose, as herein above recited, or an appropriate fraction thereof; of an active ingredient.

It should be understood that in addition to the ingredients particularly mentioned above, the formulations of this invention my include other agents conventional in the art having regard to the type of formulation in question, for example those suitable for oral administration may include flavouring agents.

The compounds of formula (I) may be prepared by various methods known in the art of organic chemistry in general. Starting materials are either known or readily available from commercial sources or may themselves be produced by known and conventional techniques.

The present invention further includes a process for the preparation of a compound of formula (I) or a physiologically functional derivative thereof. Novel chemical intermediates together with methods for their preparation are further aspects of the present invention.

Compounds of formula (I) may be prepared:

a) (wherein $R^1$ and $R^2$ are each hydrogen and m is 0) by reacting a 2-arylthio-6-nitrobenzonitrile of formula (II):

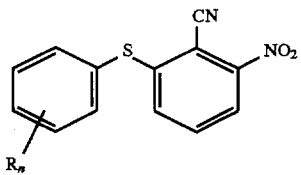

(wherein n and R are as defined for formula (I)) with a reducing agent such as $SnCl_2$ in concentrated HCl;

b) (wherein one of $R^1$ or $R^2$ is $C_{1-4}$ alkyl and the other is hydrogen, or both $R^1$ and $R^2$ are $C_{1-4}$ alkyl) by alkylation of a corresponding compound of formula (I) (wherein both $R^1$ and $R^2$ are hydrogen), for example,
  (i) by monoalkylation may be effected by first convening the amino group into an amide, such as trifluoromethyl amide, followed by alkylation of the amide and hydrolysis of the resulting product using a standard procedure to give the desired monoalkylated product; or
  ii) by dialkylation by reductive amination with the appropriate alkyl aldehydes or dialkylketones using known and conventional techniques;

c) by reacting a compound of formula (IV)

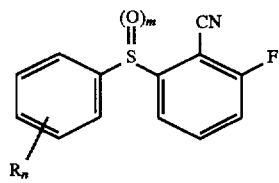

(wherein m, n and R are as defined above) with a compound of formula $HNR^1R^2$ (wherein $R^1$ and $R^2$ are as defined for formula (I);

d) (wherein m=1 or 2) by the oxidation of compounds of formula CO (wherein m=0), using for example such oxidizing agents as such as hydrogen peroxide, perbenzoic acid and OXONE (Aldrich). Such methods, however, tend to result in lower yields of products. It will be appreciated that the oxidation of compounds of formula (I) wherein m=0 to compounds of formula (I) wherein m=1 requires a proportionally smaller quantity of oxidising agent than needed for the oxidation of the same amount of a compound of formula (I) wherein m=0 to a compound of formula (I) wherein m=2.

A compound of formula (II) may be prepared by reacting a compound of formula (III)

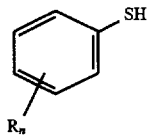

wherein $R_n$ is as defined for formula (I) with 2,6-dinitrobenzonitrile, commercially available or prepared in accordance with the method described in Harris, N. V. et al., J. Med. Chem., 1990, 33(1), 434–44, with a base such as $K_2CO_3$ in a suitable solvent such as N,N-dimethylformamide.

Compounds of formula (III) my be obtained commercially, for example, from Aldrich, Milwaukee, Wis. 53233, USA. They may also be prepared by conventional methods well known to a seed person or readily available from the chemical literature, for example J. Org. Chem. 1969, 34, 1463.

Compounds of formula (IV) where m=0 may be prepared from commercially available 2,6-difluorobenzonitrile and the appropriate arylthiol of formula (III), as described in J. Het. Chem. 1988, 25, 1173–1177. Compounds of formula (IV) where m=1 or 2 may be prepared by reacting compounds of formula (IV) where m=0 with an oxidising agent, such as those mentioned hereinabove.

Compounds of formula (IV) where m=0 may also be obtained from a one pot reaction. The initial reaction is the formation of lithium arylthiolate from the reaction of elemental sulfur and aryllithium which is obtained from the reaction of sec-butyllithium and the appropriately substituted arylbromide (lithium-halogen exchange reaction). To the resultant arylthiolate is added 2,6-difluorobenzonitrile in DMSO at 0° C. forming compounds of formula (IV) where m=0.

Pharmaceutically acceptable esters of compounds of formula (I) may be prepared by esterification of compounds of formula (II) prior to reduction, using conventional methods known in the art. Such methods include, for example, the use of an appropriate acid halide or anhydride.

The compounds of formula (I) may be convened into pharmaceutically acceptable amides by reaction with an appropriate acylating agent, for example, an acid halide or anhydride serving to acylate the phenyl amino group.

Acyl groups may be removed selectively from one or other of the hydroxyl and/or amino groups. For example, treatment of the acylated compound under acidic conditions, e.g. with a Lewis acid, such as zinc bromide in methanol, removes an N-acyl group and treatment of a diacylated compound under alkaline conditions, e.g. with sodium methoxide, removes a hydroxyl acyl group to yield an N-amide.

The compounds of formula (I), including esters and amides thereof, may be converted into pharmaceutically acceptable salts in a conventional manner. In the case of amino substituents, the salts may be obtained by treatment with an appropriate acid. In the case of amide substituents, the salts may be obtained by treatment with a base. An amide, ester or salt of a compound of formula (I) may be converted into the parent compound, for example, by hydrolysis.

The following examples are intended for illustration only and are not intended to limit the scope of the invention in any way. The term 'active ingredient' as used in the examples means a compound according to the invention.

EXAMPLE 1

2-Nitro-6-(phenylthio)benzonitrile

An ice water bath-cooled mixture of 2.0 g (0.01 mol) of 2,6-dinitrobenzonitrile (Lancaster Synthesis, Inc., Windham, N.H. 03087), 1.06 ml (0.01 mol) of thiophenol, and 1.44 g (0.01 mol) of anhydrous $K_2CO_3$ in 50 mL of DMF was stirred for 0.5 h. Pyridine was added to the reaction mixture until it became basic, and was followed by the addition of approximately 100 mL of $H_2O$. The yellow precipitate was collected by filtration, washed with 1N NaOH, water and dried to give 1.94 g (89%) of 2-nitro-6-(phenylthio)benzonitrile as a yellow solid: mp 106°–107° C.

EXAMPLE 2

2-[(3-Methoxyphenyl)thio]-6-nitrobenzonitrile

This compound was prepared according to the procedure described for Example 1. 2-[(3-methoxyphenyl)thio]-6-nitrobenzonitrile was obtained in 81% yield as a yellow solid: mp 144°–147° C.

EXAMPLE 3

2-Amino-6-(phenylthio)benzonitrile

To a water bath-cooled solution of 3.9 g (0.015 mol) of 2-nitro-6-(phenylthio)benzonitrile (Example 1) in 85 mL of diglyme was added dropwise, with stirring, 11.53 g (0.045 mol) of $SnCl_2.2H_2O$ in 35 mL of conc. HCl. The water bath was removed, and the reaction was stirred at room temperature for 0.5 h. This reaction mixture was poured into a vigorously stirring mixture of 100 mL of 50% NaOH and 300 g of crushed ice. Precipitate was collected by filtration and washed with 1N NaOH and water. Purification by flash column chromatography on silica gel with methylene chloride resulted in 2.3 g (68%) of 2-amino-6-(phenylthio) benzonitrile as a white solid: mp 73°–77° C.

EXAMPLE 4

2-Amino-6-[(3-methoxyphenyl)thio]benzonitrile

This compound was prepared according to the procedure described for Example 3. 2-Amino-6-[(3-methoxyphenyl) thio]benzonitrile was obtained in 32% yield as off-white crystals, after purification by flash column chromatography on silica gel with methylene chloride: mp 79°–81° C.

EXAMPLE 5

2-[(3,5-Dimethylphenyl)thio]-6-nitrobenzonitrile

A mixture of 2,6-dinitrobenzonitrile (1.4 g 7.2 mmol) and $K_2CO_3$ (1.1 g, 7.9 mmol) in 10 ml of DMF was chilled to 0° C. A solution of 3,5-dimethylthiophenol (1.1 g 0.0079 mmol) in 10 ml of DMF, was added dropwise over 30 min with stirring under nitrogen. After stirring an additional 30 min, the reaction mixture was poured into 150 ml of water and stirred for 1 hr. The solid was collected by vacuum filtration. Chromatography on silica gel (flash; Hex/EtOAc 1:1) provided 1.64 g (80%) of 2-[(3,5-dimethylphenyl)thio] -6-nitrobenzonitrile: mp 155°–156° C.

EXAMPLE 6

2-Amino-6-[(3,5 -dimethylphenyl)thio]benzonitrile

2-[(3,5-Dimethylphenyl)thio]-6-nitrobenzonitrile (Example 5) (1.0 g, 0.0035 mol) was dissolved in 50 ml of diglyme. A solution of stannous chloride-$2H_2O$ (3.16 g, 0.014 mol) in 15 ml of concentrated HCl was added dropwise with stirring. After stirring 1 h and 15 min, the reaction mixture was poured into a solution of 12 g NaOH in 100 ml of water with ice added to bring the total volume to 300 ml. The mixture was stirred for 1 h and the solid was collected by vacuum filtration. Chromatography on silica gel (flash; Hex/EtOAc 1:1) provided 0.57 g (64%) of 2-amino-6-[(3, 5-dimethylphenyl)thio]benzonitrile: mp 124°–125° C.; NMR ($Me_2SO-d_6$, 300 MHz) δ 2.23 (s, H), 6.17 (br, 2H), 6.24 (apparent d, 1H), 7.00 (m, 3H), 7.09 (apparent t, 1H); mass spec (CI) 255 ($M^++1$, 100%). Anal. Calc. for $C_{15}H_{14}N_2S$: C, 70.83; H, 5.55; N, 11.01; S, 12.61. Found: C, 70.84; H, 5.60; N, 10.98; S, 12.53.

Examples 7–9 were prepared by methods directly analogous to that of Example 1; Examples 10–12 were prepared by methods directly analogous to that of Example 3.

EXAMPLE 7

2-[(3-Methylphenyl)thio]-6-nitrobenzonitrile
mp 129°–130° C.

EXAMPLE 8

2-[(3-Aminophenyl)thio]-6-nitrobenzonitrile
mp 178°–179° C.

EXAMPLE 9

2-[(3,5-Dimethoxyphenyl)thio]-6-nitrobenzonitrile
mp 179°–180° C.

EXAMPLE 10

2-Amino-6-[(3 -Methylphenyl)thio]benzonitrile mp 114°–115° C.; NMR (Me$_2$SO-d$_6$, 200 MHz): δ 2.29 (s, 3H), 6.20 (br s, 2H), 6.29 (apparent d, 1H), 6.68 (apparent d, 1H), 7.23–7.15 (m, 4H), 7.31 (apparent t, 1H). Anal. Calc. for C$_{14}$H$_{12}$N$_2$S: C, 69.97; H, 5.03; N, 11.66; S, 13.34. Found: C, 69.90; H, 5.04; N, 11.59; S, 13.24.

EXAMPLE 11

2-Amino-6-[(3 -aminophenyl)thio]benzonitrile mp 99°–100° C.; NMR (Me$_2$SO-d$_6$, 200 MHz) δ 5.32 (br s, 2H), 6.17 (br s, 2H), 6.31 (apparent d, 1H), 6.50–6.70 (m, 4H), 7.07 (apparent t, 1H), 7.20 (apparent t, 1H). Anal. Calc. for C$_{13}$H$_{11}$N$_3$S.1/10 H$_2$O: C, 64.23; H, 4.64; N, 17.28; S, 13.19. Found: C, 64.06; H, 4.53; N, 17.24; S, 13.16.

EXAMPLE 12

2-Amino-6-[(3,5-dimethoxyphenyl)thio]benzonitrile mp 133°–136° C.; NMR (Me$_2$SO-d$_6$, 200MHz) δ 3.73 (s, 6H, 2×OCH$_3$), 6.25 (br s 2H), 6.52–6.44 (m, 4H), 6.75 (dd 1H), 7.26 (dd, 1H). Anal. Calc. for C$_{15}$H$_{14}$N$_2$O$_2$S: C, 62.92; H, 4.93; N, 9.78; S, 11.20. Found: C, 62.97; H, 4.96; N, 9.71; S, 11.11.

EXAMPLE 13

2-Fluoro-6-[(3 -methoxyphenyl)thio]benzonitrile

To a suspension of 10.5 g (94 mmol) of potassium t-butoxide in 140 mL of dry DMSO was added 13.1 g (94 mmol) of 3-methoxythiophenol. The resultant mixture was cooled in an ice bath. 13 g (94 mmol) of 2,6-difluorobenzonitrite was added. The resultant mixture was stirred for 15 min at ice-bath temperature followed by 45 min at RT. The mixture was poured into ice-water and basified with 1N NaOH. White precipitate was collected by filtration and dried. This precipitate was used as an intermediate for the following reactions without further purifications. Purification of 7 g by flash column chromatography on silica gel with methylene chloride/hexane (1:1) resulted in 4.59 g of pure 2-fluoro-6-[(3-methoxyphenyl)thio] benzonitrile: mp 99°–100° C.

EXAMPLE 14

2-Fluoro-6-[(3 -methoxyphenyl)sulfonyl]benzonitrile

To a solution of 2 g (7.7 mmol) of 2-fluoro-6-[(3-methoxyphenyl)thio]benzonitrile (Example 13) was added 2.93 g (17 mmol) of m-chloroperbenzoic acid. The resultant mixture was stirred for 24 h. Additional 0.29 g of m-chloroperbenzoic acid was added and the resultant mixture was stirred for 15 min. Excess sodium bisulfite was added, followed by water. The H$_2$O solution was extracted with EtOAc. After drying over MgSO$_4$ and solvent removal, the resultant crude product was purified by flash column chromatography on silica gel with methylene chloride as the fluent. This resulted in 1.15 g of 2-fluoro-6-[(3-methoxyphenyl)sulfonyl]benzonitrile as a solid: mp 113°–117° C.

EXAMPLE 15

2-Amino-6-[(3-methoxyphenyl)sulfonyl]benzonitrile

To a solution of 0.7 g (2.4 mmol) of 2-fluoro-6-[(3-methoxyphenyl)sulfonyl]benzonitrile (Example 14) in 110 ml of MeOH/EtOH (7:4) was added 20 mL of concentrated NH$_4$OH. This mixture was sealed in a glass-lined bomb and heated at 130° C. for 3 h. After solvent removal, the resultant concentrate was purified by flash column chromatography on silica gel with 5% MeOH in methylene chloride as the eluent. This resulted in 0.16 g (23%) of 2-amino-6-[(3-methoxyphenyl)sulfonyl]benzonitrile as a solid: mp 186°–191° C.; NMR (Me$_2$SO-d$_6$, 200MHz) δ 3.82 (s, 3H), 6.6 (br s, 2H), 7.1 (apparent d, 1H), 7.2–7.7 (m, 6H); mass spec (CI) 289 (M$^+$+1, 100%). Anal. Calc. for C$_{14}$H$_{12}$N$_2$O$_3$S: C, 58.32; H, 4.20;N, 9.72; S, 11.12. Found: C, 58.13; H, 4.17; N, 9.51; S, 10.95.

EXAMPLE 16

2-Fluoro-6-[(3-methoxyphenyl)sulfinyl]benzonitrile

To a solution of 2 g (7.7 mmol) of 2-fluoro-6-[(3-methoxyphenyl)thio]benzonitrile (Example 13) was added portionwise 1.6 g (9.3 mmol) of m-chloroperbenzoic acid. The resultant mixture was stirred for 24 h. Additional 0.16 g of m-chloroperbenzoic acid was added and the resultant mixture was stirred for 15 min. Excess sodium bisulfite was added, followed by water. The H$_2$O solution was extracted with EtOAc. After drying over MgSO$_4$ and solvent removal, the resultant crude product was purified by flash column chromatography on silica gel with methylene chloride as the eluent. This resulted in 1.7 g of 2-fluoro-6-[(3-methoxyphenyl)sulfinyl]benzonitrile as a solid: mp 103°–111° C.

EXAMPLE 17

2-Amino-6-[(3-methoxyphenyl)sulfinyl]benzonitrile

To a solution of 0.73 g (2.7 mmol) of 2-fluoro-6-[(3-methoxyphenyl)sulfinyl]benzonitrile (Example 16) in 65 ml of MeOH/EtOH (2.5:4) was added 20 mL of concentrated NH$_4$OH. This mixture was sealed in a glass-lined bomb and heated at 130° C. for 3 h. After solvent removal, the resultant concentrate was purified by flash column chromatography on silica gel with 5% MeOH in methylene chloride as the eluent. This resulted in 0.36 g (53%) of 2-amino-6-[(3-methoxyphenyl)sulfinyl]benzonitrile as a solid: mp 110°–114° C.; NMR. (Me$_2$SO-d$_6$, 200 MHz): δ 3.8 (s, 3H), 6.5 (br s, 2H); 7.1 (apparent d, 1H), 7.0 (apparent d, 2H), 7.2–7.3 (m, 2H), 7.5 (apparent t, 2H); mass spec (CI) 273 (M$^+$+1, 100%). Anal. Calc. for C$_{14}$H$_{12}$N$_2$O$_2$S: C, 61.75; H, 4.44; N, 10.29; S, 11.77. Found: C 61.65; H, 4.46; N, 10.21; S, 11.69.

EXAMPLE 18

2-[(3,5-Dimethylphenyl)thio]-6-fluorobenzonitrile

A mixture of 2,6-difluorobenzonitrile (2.0. g, 14 mmol) and K$_2$CO$_3$ (2.19 g, 15.8 mol) in 15 ml of DMF was chilled to 0° C. A solution of 3,5-dimethylthiophenol (2.19 g, 15.8 mol) in 15 ml of DMF, was added dropwise with slitting under nitrogen. After stirring 1 h, the reaction mixture was poured into 150 ml of water and stirred for 30 min. The solid was collected by vacuum filtration. Chromatography on silica gel (flash; Hex/EtOAc 4:1) provided 2.67 g (68%) of2-[(3,5-dimethylphenyl)thio]-6-fluorobenzonitrile: mp 98°–99° C.

EXAMPLE 19

2-[(3,5-Dimethylphenyl)sulfinyl]-6-fluorobenzonitrile

2-[(3,5-Dimethylphenyl)thio]-6-fluorobenzonitrile (Example 18) (1.0 g, 3.9 mmol) was dissolved in 100 ml of methanol. A solution of OXONE®† (2.63 g, 4.3 mmol) in 15 ml of water was added dropwise with stirring. After stirring 1.5 h, the solid was removed by vacuum filtration and washed with 3×50 ml of methanol. The filtrate was concentrated to dryness and chromatographed on silica get (flash; Hex/EtOAc 2:1) to provide 0.5 g (47%) of 2-[(3,5-dimethylphenyl)sulfinyl]-6-fluorobenzonitrile: mp 146°–147° C.

†OXONE® $2KHSO_5 \cdot KHSO_4 K_2SO_4$

EXAMPLE 20

2-[(3,5-Dimethylphenyl)sulfonyl]-6-fluorobenzonitrile

2-[(3,5-Dimethylphenyl)thio]-6-fluorobenzonitrile (Example 18) (1.0 g 3.9 mmol) was dissolved in 100 ml of methanol. A solution of OXONE®† (5.26 g, 8.6 mmol) in 30 ml of water was added dropwise with stirring. After stirring 1 h, another 1.5 equivalents of OXONE® (3.60 g 5.9 mmol) was added. The reaction was stirred for 18 h. The solid was removed by vacuum filtration and washed with 200 ml of methanol, then with 2×60 ml of acetone. The filtrate was concentrated to dryness and chromatographed on silica gel (flash; Hex/EtOAc 1:1) to provide 0.73 g (65%) of 2-[(3,5-dimethylphenyl)sulfonyl]-6-fluorobenzonitrile: mp 167°–168° C.

EXAMPLE 21

2-4-Amino-6-[(3,5-dimethylphenyl)sulfinyl]benzonitrile

2-[(3,5-Dimethylphenyl)sulfinyl]-6-fluorobenzonitrile (Example 19) (0.4 g, 1.5 mmol) was dissolved in 40 ml of methanol and chilled to −78° C. Condensed ammonia (20 ml, 15.4 g, 905 mmol) was added and the mixture was heated to 150° C. in a sealed Parr bomb for 24 h. Chromatography on silica gel (flash; Hex/EtOAc 1:1) provided 0.24 g (61%) of 2-amino-6-[(3,5-dimethylphenyl)sulfinyl] benzonitrile: mp 190°–191° C.; NMR ($Me_2SO-d_6$, 200 MHz) δ 2.32 (s, 6H), 6.48 (br s, 2H), 6.90 (apparent d, 1H), 7.11 (apparent d, 1H), 7.20 (m, 1H), 7.32 (m, 2H), 7.52 (apparent t, 1H); mass spec (CI) $M^++1=271$. Anal. Calc. for $C_{15}H_{14}N_2OS$: C, 66.64; H, 5.22; N, 10.36; S, 11.86. Found: C, 66.71; H, 5.27; N, 10.32; S, 11.84.

EXAMPLE 22

2-Amino-6-[(3,5-dimethylphenyl)sulfonyl]benzonitrile

2-[(3,5-Dimethylphenyl)sulfonyl]-6-fluorobenzonitrile (Example 20) (0.5 g 1.7 mmol) was dissolved in 80 ml of methanol and chilled to −78° C. Condensed ammonia (20 ml, 15.4 g, 905 mmol) was added and the mixture was heated to150° C. in a sealed Parr bomb for 24 h. Chromatography on silica gel (flash; Hex/EtOAc 1:1) provided 0.28 g (56%) of 2-amino-6-[(3,5-dimethylphenyl)sulfonyl] benzonitrile: mp 208°–209° C.;; NMR ($Me_2SO-d_6$, 200 MHz) δ 2.36 (s, 6H), 6.59 (br s, 2H), 7.10 (apparent d, 1H), 7.3–7.4 (m, 2H) 7.54 (apparent d, 1H), 7.58 (m, 2H); mass spec (CI) $M^++1=287$. Anal. Calc. for $C_{15}H_{14}N_2O_2S$: C, 62.92; H, 4.93; N: 9.78; S, 11.20. Found: C, 63.02; H, 4.98; N, 9.72; S, 11.12.

EXAMPLE 23

2-Fluoro-6-[(3 -methyl-5-methoxyphenyl)thio]benzonitrile

A solution of 1 g (0.005 mol) of 3-bromo-5-methoxytoluene in 10 mL of freshly distilled THF was cooled in dry ice/acetone and stirred under a $N_2$ atmosphere. To this was added dropwise via a syringe 8.46 mL (0.011 mol) of sec-BuLi (1.3M in cyclohexane). The resultant mixture was stirred for 10 min after which 0.19 g of elemental sulfur was added in one portion. The reaction mixture was brought to room temperature and left stirring for 12 h. The mixture was cooled in ice/water bath. 0.69 g (0.005 mol) of 2,6-difluorobenzonitrile in 5 mL of dry DMSO was added. After sitting for 20 min, the mixture was poured into water (100 mL) and extracted with 3×50 mL of EtOAc. The EtOAc solution was washed with 1N NaOH, water, and dried over $MgSO_4$ Removal of EtOAc under vacuo resulted in a crude product which was chromatographed on silica gel (flash; EtOAc/Hexane 1:9). This resulted in 0.63 g (46%) of 2-fluoro-6-[(3-methyl-5-methoxyphenyl)thio]benzonitrile: mp 94°–95° C.; NMR ($Me_2SO-d_6$, 200 MHz) δ 2.28 (s, 3H), 3.7 (s, 3H), 6.8–7 (m, 4H), 7.34 (apparent d, 1H), 7.62 (dd, 1H). Anal. Calc. for $C_{15}H_{12}NOSF$: C, 65.92; H, 4.43; N, 5.12; S, 11.73. Found: C, 66.03; H, 4.49; N, 5.09; S, 11.8.

EXAMPLE 24

2-Amino-6-[(3 -methyl-5-methoxyphenyl)thio]benzonitrile

A solution of 0.1 g (0.00037 mol) of 2-fluoro-6-[(3-methyl-5-methoxyphenyl)thio]benzonitrile (Example 23) in 10 mL of absolute ethanol and ca. 2 mL of THF was saturated with ammonia. The resultant solution was sealed in a glass-lined Parr bomb and heated to 145° C. for 48 h. The solvent was removed in vacuo. 20 mL of 1 NaOH was added. This aqueous solution was extracted with 3×20 mL of EtOAc. The EtOAc solution was dried over $MgSO_4$. After solvent removal, the crude product was chromatographed on silica gel (flash; $CH_2Cl_2$), resulting in 0.03 g (30%) of 2-amino-6-[(3-methyl-5-methoxyphenyl)thio]benzonitrile as a white solid: mp 108°–110° C.; NMR ($Me_2SO-d_6$, 200 MHz) δ 2.32 (s, 3H), 3.78 (s, 3H), 6.28 (br s, 1H), 6.4 (apparent d, 1H), 6.7–6.8 (m, 2H), 6.8–6.9 (narrow m, 2H), 7.28 (apparent d, H). Anal. Calc. for $C_{15}H_{14}N_2OS$: C, 66.64; H, 5.22; N, 10.36; S, 11.36. Found: C, 66.46; H, 5.22; N, 10.25; S, 11.71.

EXAMPLE 25

2-Fluoro-6-[(3 -methyl-5-methoxyphenyl)sulfonyl] benzonitrile

A mixture of 0.4 g (0.0015 mol) of 2-fluoro-6-[(3-methyl-5-methoxyphenyl)thio]benzonitrile (Example 23) and 0.76 g (0.0044 mol) of m-chloroperbenzoic acid in 20 ml, of $CH_2Cl_2$ was stirred for 16 h. The precipitate formed was faltered. The filtrate was diluted with 50 mL of EtOAc. This was washed with saturated $NaHSO_3$, 1N NaOH, and water. After drying over $MgSO_4$, the solvent was removed, resulting in 0.38 g (83%) of 2-fluoro-6-[(3-methyl-5-methoxyphenyl)-sulfonyl]benzonitrile as a white solid: mp 160°–162° C.; NMR ($Me_2SO-d_6$, 200MHz) δ 2.34 (s, 3H), 3.80 (s, 3H), 7.17 (s, 1H) 7.34 (apparent d, 2H) 7.9 (apparent t, 1H), 8.0–8.1 (m, 1H), 8.15 (apparent d, 1H). Anal. Calc. for $C_{15}H_{12}NO_3SF$: C, 59.01; H, 3.96; N, 4.59; S, 10.50. Found: C, 59.12; H, 4.03; N, 4.49; S, 10.43.

EXAMPLE 26

2-Amino-6-[(3-methyl-5-methoxyphenyl)sulfonyl] benzonitrile

A solution of 0.3 g (0.00098 mol) of 2-fluoro-6-[(3-methyl-5-methoxyphenyl)sulfonyl]benzonitrile (Example 25) in 10 mL of absolute ethanol and ca. 2 mL of THF was saturated with ammonia. The resultant solution was sealed in a glass-lined Parr bomb and heated to 130° C. for 4 h. The solvent was removed in vacuo. 20 mL of 1 NaOH was added. This aqueous solution was extracted with 3×50 mL of EtOAc. The EtOAc solution was dried over $MgSO_4$. After solvent removal, the crude product was recrystallized from absolute ethanol to give 0.1 g (34%) of 2-amino-6-[(3-methyl-5-methoxyphenyl)sulfonyl]benzonitrile: mp 166°–168° C.; NMR ($Me_2SO-d_6$, 200 MHz $\delta$ 2.4 (s, 3H), 3.87 (s, 3H), 6.7 (br s, 2H), 7.13 (apparent d, 1H), 7.2 (unresolved s, 1H), 7.3–7.5 (m, 2H), 7.57 (apparent t, 1H). Anal. Calc. for $C_{15}H_{14}N_2O_3S$: C, 59.59; H, 4.67;N, 9.27; S, 10.6. Found: C, 59.67;H, 4.71;N, 9.25; S, 10.51.

EXAMPLE 27

Tablet Formulations

The following formulations A, B and C are prepared by wet granulation of the ingredients with a solution of povidone, followed by the addition of magnesium stearate and compression.

Formulation A

|  | mg/tablet | mg/tablet |
|---|---|---|
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |

Formulation B

|  | mg/tablet | mg/tablet |
|---|---|---|
| (a) Active ingredient | 250 | 250 |
| (b) Lactose | 150 | — |
| (c) Avicel PH 101 | 60 | 6 |
| (d) Povidone B.P. | 5 | 9 |
| (e) Sodium Starch Glycollate | 20 | 12 |
| (f) Magnesium Stearate | 5 | 3 |
|  | 500 | 300 |

Formulation C

|  | mg/tablet |
|---|---|
| Active ingredient | 100 |
| Lactose | 200 |
| Starch | 50 |
| Povidone | 5 |
| Magnesium Stearate | 4 |
|  | 359 |

The following formulations, D and E, are prepared by direct compression of the admixed ingredients. The lactose in formulation E is of the direct compression type (Dairy Crest—"Zeparox").

Formulation D

|  | mg/tablet |
|---|---|
| Active ingredient | 250 |
| Pregelatinised Starch NF15 | 150 |
|  | 400 |

Formulation E

|  | mg/tablet |
|---|---|
| Active ingredient | 250 |
| Lactose | 150 |
| Avicel | 100 |
|  | 500 |

Formulation F (Controlled Release Formulation)

The formulation is prepared by wet granulation of the ingredients (below) with a solution of povidone followed by the addition of magnesium stearate and compression.

|  | mg/tablet |
|---|---|
| (a) Active ingredient | 500 |
| (b) Hydroxypropylmethylcellulose (Methocel K4M Premium) | 112 |
| (c) Lactose B.P. | 53 |
| (d) Povidone B.P. | 28 |
| (e) Magnesium Stearate | 7 |
|  | 700 |

Drag release takes place over a period of about 6–8 hours and is complete after 12 hours.

EXAMPLE 28

Capsule Formulations
Formulation A

A capsule formulation is prepared by admixing the ingredients of Formulation D in Example 2 above and filling the mixture into a two-part hard gelatin capsule. Formulation B (infra) is prepared in a similar manner.

Formulation B

|  | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
|  | 420 |

Formulation C

|  | mg/capsule |
|---|---|
| (a) Active ingredient | 250 |
| (b) Macrogol 4000 B.P. | 350 |
|  | 600 |

Formulation D

|  | mg/capsule |
| --- | --- |
| Active ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extradate and drying. The dried pellets are then coated with the release-controlling membrane (d) and filled into a two-piece, hard gelatin capsule.

|  | mg/capsule |
| --- | --- |
| (a) Active ingredient | 250 |
| (b) Microcrystalline Cellulose | 125 |
| (c) Lactose B.P. | 125 |
| (d) Ethyl Cellulose | 13 |
|  | 513 |

EXAMPLE 29

Injectable Formulation
Formulation A

| Active ingredient | 0.200 g |
| --- | --- |
| Hydrochloric acid solution, 0.1M, or | |
| Sodium hydroxide solution, 0.1M q.s. to pH 4.0 to 7.0 | |
| Sterile water q.s. to | 10 ml |

The active ingredient is dissolved in most of the water at 35° C.–40° C. and the pH adjusted to between 4.0 and 7.0 with the hydrochloric acid or sodium hydroxide as appropriate. The batch is then made up to volume with the water and filtered through a sterile micropore filter into a sterile 10 ml amber glass vial (type 1) and sealed with sterile closures and overseals.

Formulation B

| Active ingredient | 0.125 |
| --- | --- |
| Sterile, pyrogen-free, pH 7 phosphate buffer, q.s. to | 25 ml |

EXAMPLE 30

Intramuscular injection

| Active ingredient | 0.20 g |
| --- | --- |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is filtered through a sterile micropore filter and sealed in sterile 3 ml amber glass vials (type 1).

EXAMPLE 31

Syrup

| Active ingredient | 0.25 g |
| --- | --- |
| Sorbitol Solution | 1.50 g |
| Glycerol | 2.00 g |
| Sodium Benzoate | 0.005 g |
| Flavor, Peach | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

Formulation B

| Active ingredient | 0.125 g |
| --- | --- |
| Sterile, pyrogen-free, pH 7 phosphate buffer, q.s. to | 25 ml |

EXAMPLE 32

Suppository

|  | mg/suppository |
| --- | --- |
| Active ingredient (631 m)* | 250 |
| Hard Fat, B.P. (Witepsol H15 - Dynamit NoBel) | 1770 |
|  | 2020 |

*The active ingredient is used as a powder wherein at least 90% of the particles are of 631 m diameter or less. One-fifth of the Witepsol H15 is melted in a steam-jacketed pan at 45° C. maximum. The active ingredient is sifted through a 200 µm sieve and added to the molten base with mixing, using a Silverson fitted with a cutting head, until smooth dispersion is achieved. Maintaining the mixture at 45° C., the remaining Witepsol H15 is added to the suspension and stirred to ensure a homogenous mix. The entire suspension is passed through a 250 µm stainless steel screen and, with continuous stirring, allowed to cool to 40° C. At a temperature of 38° C. to 40° C., 2.0 g of the mixture is filled into suitable 2 ml plastic moulds. The suppositories are allowed to cool to room temperature.

*The active ingredient is used as a powder wherein at least 90% of the particles are of 631 m diameter or less. One-fifth of the Witepsol H15 is melted in a steam-jacketed pan at 45° C. maximum. The active ingredient is sifted through a 200 µm sieve and added to the molten base with mixing, using a Silverson fitted with a cutting head, until smooth dispersion is achieved. Maintaining the mixture at 45° C., the remaining Witepsol H15 is added to the suspension and stirred to ensure a homogenous mix. The entire suspension is passed through a 250 µm stainless steel screen and, with continuous stirring, allowed to cool to 40° C. At a temperature of 38° C. to 40° C., 2.0g of the mixture is filled into suitable 2 ml plastic moulds. The suppositories are allowed to cool to room temperature.

EXAMPLE 33

Pessaries

|  | mg/pessary |
|---|---|
| Active ingredient (631 m) | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 34

Antiviral Activity
HIV Assay

Anti-HIV activity of compounds of the invention was determined using the method of Averett D. R., J. Virol. Methods, 1989, 23, 263–276, by measuring the ability of the compound to reverse the cytopathic effect of HIV infection. This was determined by a quantitative assessment of cell growth monitored at the fifth day post infection by a propidium iodide dye uptake test. MT4 cells were incubated with 100XTCID$_{50}$ HIV-1 (strain 3B) or HIV-2 (strain ZY) for one hour prior to addition of the compound in six different concentrations varying from 2 to 200 µM. The cells were allowed to incubate for five days at 37° C. On day 5, NP-40, a detergent, was added to a final concentration of 0.5% immediately prior to analysis. Cell number was determined using a method which measures the fluorescence of a dye (propidium iodide) which binds to DNA. Since the amount of DNA is directly proportional to cell number, this fluorescence assay is an indication of cell growth. While uninfected cells double in cell number several times during the five days duration of the assay, HIV-infected cells grow very little, if at all. A compound which reverses the cyzopathic effect of HIV would allow for rapid cell growth, approaching that of the mock-infected cells.

The antiviral effect of a compound is reported as an IC$_{50}$, i.e. as the inhibitory concentration that would produce a 50% decrease in the HIV-induced cytopathic effect. This effect is measured by the mount of compound required to restore 50% of the cell growth of HIV-infected MT4 cells, compared to uninfected MT4 cell controls.

| Anti-HIV-1 Activity of Compounds | |
|---|---|
| Compound | IC$_{50}$ (µM) |
| Example 3 | 14.6 ± 2.6; 17.9 ± 2.9 |
| Example 4 | 6.84 ± 1.00; 5.44 ± 0.27 |
| Example 6 | 0.432 ± 0.078 |
| Example 15 | 0.92 ± 0.04 |
| Example 17 | 15.9 ± 1.3 |
| Example 22 | 0.014 ± 0.001 |

EXAMPLE 35

Anti-inflammatory Activity
Carrageenan Pleurisy Assay

The antiinflammatory activity of compounds of the invention was determined by the procedure of Vinegar, R. et al., Proc. Soc. Exp. Biol. Med., 1981, 168, 24–32, using male Lewis rats of 150±20 grams. The carrageenan dose was 0.075 mg/rat. Pleural exudate was harvested four hours after injection of carageenan. Acute an antiiflammatory activity was determined by inhibition of pleural edema and inflammatory cells (neutrophils) from a negative (vehicle) control group.

Acute Anti-inflammatory Activity of Compounds in the 4 Hour Carageenan Pleurisy Assay in Rats

|  | % INHIBITION* @ 25 MG/KG (IP) | | @ 50 MG/KG (PO) | |
|---|---|---|---|---|
| COMPOUND | CELLS | EDEMA | CELLS | EDEMA |
| Example 17 | 40% | 57% | 19% | 7% |
| Example 21 | 37% | 42% | 28% | 24% |
| Example 22 | 0% | 5% | 29% | 31% |

*relative to solvent (vehicle) control animals

EXAMPLE 36

Cytotoxicity

Compounds of the invention were tested for the inhibition of growth of human T-cells (Molt 4), B-cells (IM9) and CEM cells by the method of Averett, D. R., J. Virol. Methods, 23, 263–276 (1989). Cells were grown as described in Prus, K. L., et al., Cancer Res., 50(6), 1817–1821 (1990). Results are as follows:

|  | % of Cells Surviving at 100 µM | | |
|---|---|---|---|
| Compound | IM9 | CEM | Molt4 |
| Example 22 | 97 | 70 | 91 |

I claim:

1. A compound of formula (I)

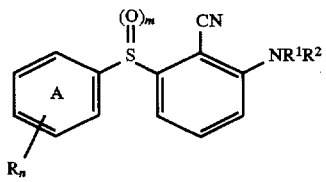

wherein,

R is hydrogen, C$_{1-4}$ alkyl, C$_{1-4}$ alkoxy, hydroxyl, mercapto, NR$^{1a}$R$^{2a}$ (wherein R$^{1a}$ and R$^{2a}$, which may be the same or different are, phenyl C$_{1-4}$ alkyl) or SR$^{1a}$ (wherein R$^{1a}$ is hydrogen, C$_{1-4}$alkyl or phenyl C$_{1-4}$ alkyl;

R$^1$ and R$^2$, which may be the same or different, are hydrogen, C$_{1-4}$ alkyl or phenyl C$_{1-4}$ alkyl;

m is 0, 1 or 2 and;

n is 1 to 5 (when n is greater than 1, R may be the same or different);

provided that when R$^1$ and R$^2$ are both hydrogen and m is 0, R is not hydrogen, or a physiologically functional derivative thereof.

2. A compound according to claim 1 wherein n is 1 or 2, ring A is 3-substituted or 3,5-disubstituted and m is 2.

3. A compound according to claim 1 which is selected from the group consisting of:

2-amino-6-[(3-methoxyphenyl)thio]benzonitrile;
2-amino-6-[(3-methylphenyl)thio]benzonitrile;
2-amino-6-[(3,5-dimethylphenyl)thio]benzonitrile;
2-amino-6-[(3-aminophenyl)thio]benzonitrile;

2-amino-6-[(3,4-dimethoxyphenyl)thio]benzonitrile;
2-amino-6-[(3-methoxyphenyl)sulfonyl]benzonitrile;
2-amino-6-[(3-methoxyphenyl)sulfinyl]benzonitrile;
2-amino-6-[(3,5-dimethylphenyl)sulfinyl]benzonitrile;
2-amino-6-[(3,5-dimethylphenyl)sulfonyl]benzonitrile;
2-amino-6-[(3-methyl-5-methoxyphenyl)sulfonyl]benzonitrile;
2-amino-6-[(3-methyl-5-methoxyphenyl)thio]benzonitrile; and
2-(benzylamino)-6-[(3,5-dimethylphenyl)sulfonyl]benzonitrile;

or a physiologically functional derivative thereof.

4. 2-Amino-6-[(3,5-dimethylphenyl)sulfonyl]benzonitrile.

5. A compound of formula (I)

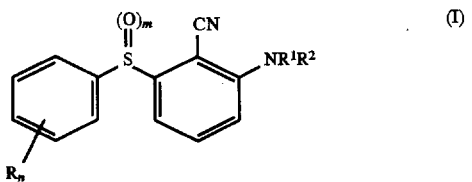

wherein,

R is hydrogen, $C_{1-4}$ alkyl, $C_{1-4}$ alkoxy, hydroxyl, mercapto, $NR^{1a}R^{2a}$ (where $R^{1a}$ and $R^{2a}$, which may be the same or different are, phenyl $C_{1-4}$ alkyl) or $SR^{1a}$ (wherein $R^{1a}$ is hydrogen, $C_{1-4}$ alkyl or phenyl $C_{1-4}$ alkyl;

$R^1$ and $R^2$, which may be the same or different, are hydrogen, $C_{1-4}$ alkyl or phenyl $C_{1-4}$ alkyl;

m is 0, 1 or 2 and;

n is 1 to 5 (when n is greater than 1, R may be the same or different);

provided that when $R^1$ and $R^2$ are both hydrogen and m is 0, R is not hydrogen, or a physiologically acceptable derivative thereof for use in medical therapy.

6. A compound according to claim 5 for use in antiviral therapy.

7. A compound according to claim 5 for use in the treatment or prophylaxis of inflammation.

8. A method for the treatment or prophylaxis of a viral infection or inflammation which comprises administering a therapeutically effective non-toxic amount of a compound of formula (I) as defined in claim 5 or a physiologically acceptable derivative thereof.

9. A method for the prophylaxis or treatment of a viral infection in an infected host which comprises administering to said host a therapeutically effective non-toxic amount of a compound of formula (I) as defined in claim 5 or a physiologically acceptable derivative thereof.

10. A method for the prophylaxis or treatment of intimation in an affected host which comprises administering to said host a therapeutically effective non-toxic amount of a compound of formula (I) as defined in claim 5 or a physiologically acceptable derivative thereof.

11. A pharmaceutical formulation which comprises a compound of formula (I) according to claim 1 together with a pharmaceutically acceptable carrier therefor.

12. A pharmaceutical formulation as claimed in claim 11 in the form of a tablet or a capsule.

13. A process for the preparation of compounds of formula (I) as defined in claim 1 or a physiologically functional derivative thereof which comprises;

a) (wherein $R^1$ and $R^2$ are each hydrogen and m is 0) reacting a compound of formula (II)

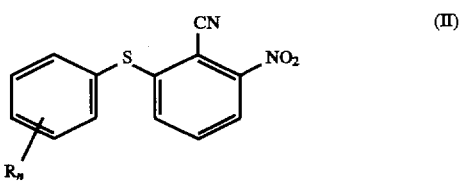

(wherein n and R are as defined in claim 1) with a reducing agent;

b) (wherein one of $R^1$ or $R^2$ is $C_{1-4}$ alkyl and the other is hydrogen or both $R^1$ and $R^2$ are $C_{1-4}$ alkyl) by alkylating a corresponding compound of formula (I) wherein both $R^1$ and $R^2$ are hydrogen;

c) reacting a compound of formula (IV)

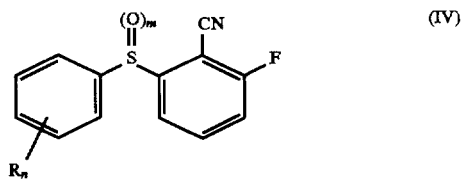

wherein m, n and R are as defined above, with a compound of formula $HNR^1R^2$ (wherein $R^1$ and $R^2$ are as defined in claim 1)

d) ( wherein m=1 or 2) reacting a compound of formula (I) wherein m=0 with an oxidising agent.

14. A process as claimed in claim 13 for the preparation of 2-amino-6-[(3,5-dimethylphenyl)sulfonyl]benzonitrile.

* * * * *